United States Patent [19]
Banjanin et al.

[11] Patent Number: 5,443,071
[45] Date of Patent: Aug. 22, 1995

[54] QUANTITATIVE COLOR FLOW

[75] Inventors: Zoran B. Banjanin, Renton; Jin Kim, Issaquah, both of Wash.

[73] Assignee: Siemens Medical Systems, Inc., Iselin, N.J.

[21] Appl. No.: 322,113

[22] Filed: Oct. 11, 1994

[51] Int. Cl.$^6$ .............................................. A61B 8/00
[52] U.S. Cl. .............................. 128/661.09; 73/861.25
[58] Field of Search ...................... 128/661.08, 661.09, 128/661.10; 73/861.25, 861.26

[56] References Cited

U.S. PATENT DOCUMENTS

| | | | |
|---|---|---|---|
| 5,010,528 | 4/1991 | Ohtsuki et al. | 128/661.09 |
| 5,190,044 | 3/1993 | Kawasaki et al. | 128/661.09 |
| 5,287,753 | 2/1994 | Routh et al. | 73/861.25 |

*Primary Examiner*—George Manuel

[57] ABSTRACT

Method for providing a quantitative color flow display of moving matter using an ultrasound imaging system, the display being formed of pixels on a display device, which method includes the steps of: (a) transmitting acoustic beams to a region of interest in the body, which region of interest includes the moving matter; (b) receiving echo beams from the region of interest; (c) obtaining, at each portion of the region of interest, which portion is referred to as a pixel, a measure of velocity of moving matter in the pixel and a measure of direction of the velocity of the moving matter in the pixel; (d) determining a maximum of the measure of velocity at each pixel in the region of interest over a predetermined period of time and the measure of direction of the maximum velocity; and (e) displaying the measures of velocity of the pixels for the predetermined period of time wherein the measures of velocity and the measure of direction of the velocity are displayed using a color indicator which is relative to the maximum measure of velocity at each pixel and to the measure of direction of the maximum velocity.

23 Claims, 6 Drawing Sheets

QUANTITATIVE COLOR FLOW

TECHNICAL FIELD OF THE INVENTION

The present invention relates to ultrasound imaging systems using Doppler flow imaging and, in particular, to method and apparatus for quantitative color flow measurement and display of moving matter.

BACKGROUND OF THE INVENTION

It is known that a medical ultrasound imaging system can be used to display and analyze anatomical structures within a patient's body. The ultrasound imaging system transmits sound waves of very high frequency, typically 2 to 10 MHz, into the patient's body and processes echoes reflected from tissues and materials within the patient's body. A number of different types of displays are provided by ultrasound imaging systems but probably the most popular display is a two-dimensional image of selected cross-sections of the body. In an echo mode of operation, all echoes from a selected cross-section are processed and displayed. Use of the echo mode of operation enables a sonographer to detect a number of anatomical defects. Further, the size of such defects can be more or less precisely determined. The performance of the echo mode of operation is determined by the size of a resolution cell and, as is well known, the size of a resolution cell can be decreased by utilizing dynamic focusing and dynamic (matched) filtering.

In some clinical applications, anatomical defects can be relatively small, and echoes produced by such small anatomical defects are overshadowed by larger echoes from surrounding tissue. However, such small anatomical defects may be seen by displaying changes in blood flow velocity. As is well known, Doppler measurements can be used to determine the velocity of a moving object and a display of Doppler shifts caused by blood flow enables small anatomical defects to be detected more easily. This mode of operation wherein Doppler shifts caused by blood flow are displayed is known in the art as Color Flow. For example, U.S. Pat. No. 4,800,891 describes the Color Flow process and describes how Doppler information relating to blood flow velocity can be gathered from a large, selected cross-section of an anatomical structure. Modern Color Flow processors used in ultrasound imaging systems output estimates of three spectral moments of a flow signal, power, velocity, and variance and ultrasound imaging system displays typically provide information related to power or velocity.

It is difficult to acquire sufficient ultrasound data to develop an accurate, high resolution, blood flow image at a high rate. Thus, in order to obtain more precise Doppler information about blood flow velocity from a small cross-section area, as is well known, a spectral Doppler mode of operation is used. In the spectral Doppler mode of operation it is possible to devote more time to a selected small area. The results of the spectral Doppler mode of operation are conventionally displayed by means of a frequency spectrum and an audio signal.

Current ultrasound imaging systems providing a spectral Doppler mode of operation and a Color Flow mode of operation suffer from an inherent defect. Such current ultrasound imaging systems measure blood flow velocity in a blood vessel of interest by using a Doppler frequency shift which is obtained by analyzing echoes received from a region of interest from one receive beam direction. However, as is known, blood flow velocity measured in this way is a function of the angle of blood flow with respect to an ultrasound transmit beam. Thus, in the absence of information about the blood flow angle, the measured blood flow velocity is only a projection of the true blood flow velocity in the direction of the ultrasound transmit beam. In order to overcome this deficiency in the Spectral Doppler mode of operation, an operator, i.e., a sonographer, has to adjust the ultrasound transmit beam manually to align it with the direction of blood flow in the blood vessel to obtain a more accurate measurement of blood flow velocity. As one can readily appreciate, manual angle correction of blood flow velocity is only applicable to the Spectral Doppler mode, is cumbersome, and is hard to use to make repeated measurements having the same angle.

As is well known, to obtain the blood flow angle, one needs to receive echoes from a region of interest from more than one direction. Several proposals have been made in the past to solve this problem using multiple beam configurations. However, most of these proposed techniques require multiple transmit and multiple receive beams, all of which complicate transducer functionality and are, therefore, not practical for use in a clinical setting. These multiple beam configurations suffer from an additional problem in that they have to be adjusted to insonify the same region within a blood vessel.

Another technique is described in an article entitled "Angle Independent Ultrasonic Detection of Blood Flow" by G. E. Trahey, J. W. Allison, and O. T. von Ramm, *IEEE Trans. Biomed. Eng.*, vol. BME-34, pp. 965–967, December 1987. This technique is based on tracking motion of a speckle pattern produced by blood to achieve flow direction information. The technique relies on a two-dimensional search of a Doppler image and is, therefore, computationally very intense. For that reason, the technique is not considered to be practical for real time Doppler modes of operation.

More recently a proposal has been made for another technique that comprises: (a) sonifying a sample volume with one transmit beam and (b) detecting two receive beams from two angles. This technique is disclosed in an article entitled "Vector Doppler: Accurate Measurement of Blood Velocity in Two Dimensions" by J. R. Overbeck, K. W. Brach, and D. E. Strandness, *Ultrasound in Medicine and Biology*, vol. 18, No. 1, pp. 19–31, 1992. In the disclosed technique, a first transducer is used to generate a transmit beam and a second and a third transducer, disposed on either side of the first transducer element, are used to detect receive beams at the same angle with respect to the transmit beam. The technique suffers in that it is limited to a specific transducer configuration and it utilizes a fast-fourier-transform-based mean frequency estimator which makes the disclosed method inaccurate or complicated.

Lastly, a proposal has been made by P. J. Phillips of Duke University in 1992 for still another technique that comprises: (a) sonifying a sample volume with one transmit beam and (b) receiving two receive beams from two angles. In this technique, the transducer aperture is divided into two sub-apertures. A transmit beam is generated at one sub-aperture and a receive beam is detected at the same sub-aperture. Next, a transducer beam is again generated at the same sub-aperture and a receive beam is detected at the other sub-aperture.

In light of the above, there is a need in the art for a method for determining blood flow angle in an ultrasound imaging system and for using this result to provide a quantitative color flow mode of operation.

SUMMARY OF THE INVENTION

Advantageously, embodiments of the present invention solve the above-identified need in the art by providing a method for determining blood flow angle in an ultrasound imaging system and for using this result to provide a quantitative color flow mode of operation.

In particular, an embodiment of the present invention is a method for providing a quantitative color flow display of moving matter using an ultrasound imaging system, the display being formed of pixels on a display device, which method comprises the steps of: (a) transmitting acoustic beams to a region of interest in the body, which region of interest includes the moving matter; (b) receiving echo beams from the region of interest; (c) obtaining, at each portion of the region of interest, which portion is referred to as a pixel, a measure of velocity of moving matter in the pixel and a measure of direction of the velocity of the moving matter in the pixel; (d) determining a maximum of the measure of velocity at each pixel in the region of interest over a predetermined period of time and the measure of direction of the maximum velocity; and (e) displaying the measures of velocity of the pixels for the predetermined period of time wherein the measures of velocity and the measure of direction of the velocity are displayed using a color indicator which is relative to the maximum measure of velocity at each pixel and to the measure of direction of the maximum velocity.

DETAILED DESCRIPTION

Figure 1:
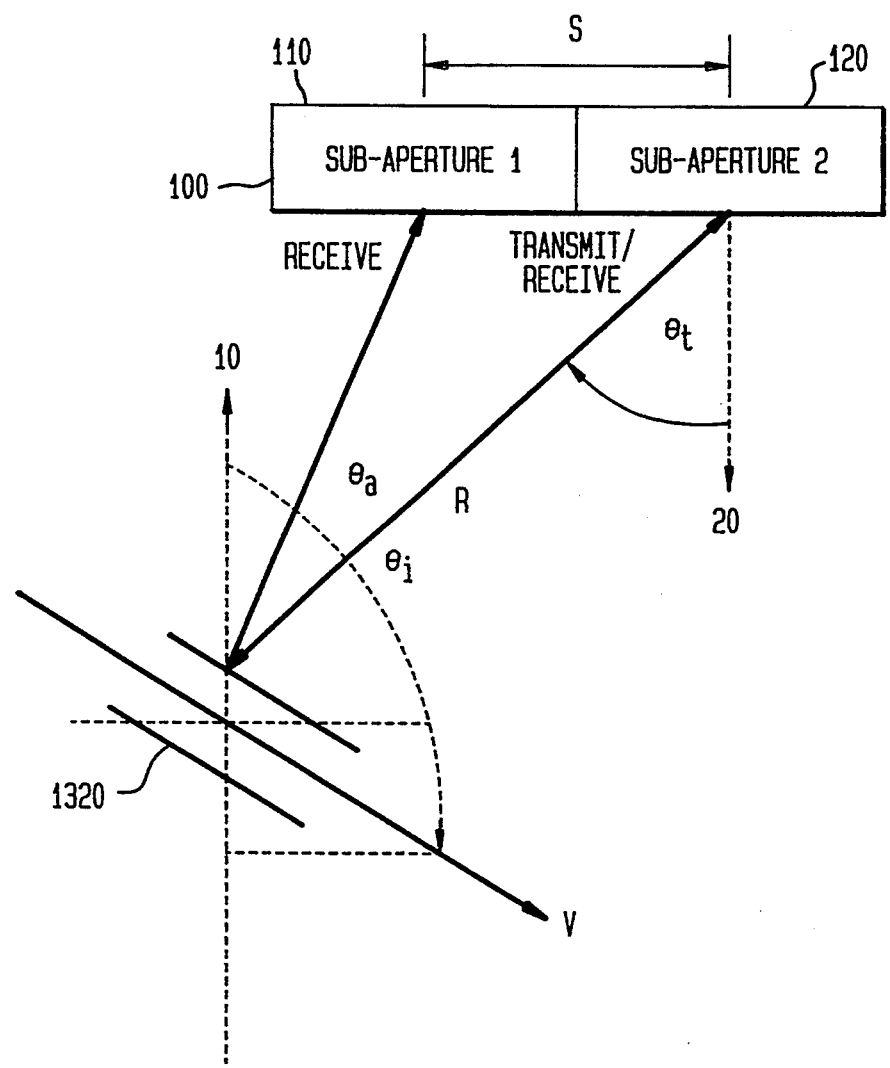
FIG. 1 shows, in pictorial form, a transducer array arrangement for transmit and receive beam geometries used to fabricate embodiments of the present invention in an ultrasound imaging system.

FIG. 1 shows, in pictorial form, a transducer array arrangement for transmit and receive beam geometries used to fabricate embodiments of the present invention in an ultrasound imaging system. As shown in FIG. 1, blood vessel 1320 has blood flowing therethrough with velocity V at an angle $\Theta_i$ with respect to arrow 10. In accordance with a preferred embodiment of the present invention, transducer array 100 is broken down into sub-apertures 110 and 120. A single transmit beam is generated from sub-aperture 120 and receive beams are detected by sub-apertures 110 and 120. Sub-aperture 110 receives echoes caused by angular scattering and sub-aperture 120 receives echoes caused by backscattering.

As further shown in FIG. 1, the centers of sub-apertures 110 and 120 are separated by a predetermined distance S and R defines the distance between the center of sub-aperture 120 and a sample volume in the blood vessel of interest. In the preferred embodiment, transducer array 100 is a linear phased array and it is divided into two, equal sub-aperture arrays in a manner which is well known to those of ordinary skill in the art. For example, for a 64-element transducer array, each sub-aperture array will contain 32 elements. Further, each sub-aperture array is independently steered and focused. Methods for dividing full-aperture transducer array 100 into two, equal sub-aperture arrays 110 and 120 that can be steered, focused and that can receive simultaneously are well known in the art.

Figure 2:
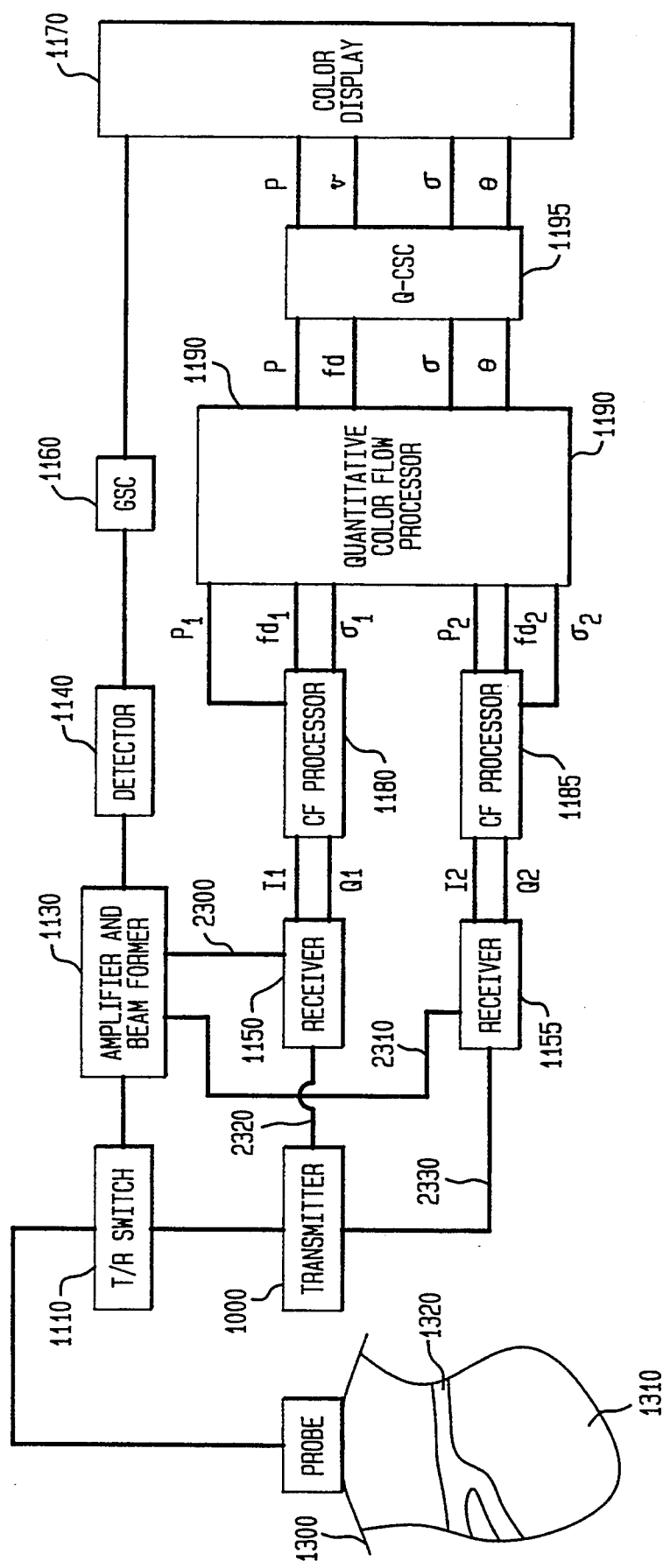
FIG. 2 shows a block diagram of an embodiment of the present invention.

FIG. 2 shows a block diagram of an embodiment of the present invention. Referring to FIG. 2, transmitter 1000 produces a signal at a desired ultrasound frequency for generating a transmit beam from sub-aperture 120 of ultrasound probe 1120. The signal is amplified and applied as input to ultrasound probe 1120 (which contains transducer array 100) through transmit/receive switch 1110 (T/R switch 1110). As is known in the art, T/R switch 1110 provides isolation of sensitive amplifying circuitry in amplifier and beamformer 1130 (AB 1130) while transmit beams are generated. Sub-aperture 120 of ultrasound probe 1120 converts electrical pulse signals from transmitter 1100 into ultrasonic pulsed waves which are transmitted into scanned body 1300.

As shown in FIG. 2, scanned body 1300 is comprised of tissue 1310 and blood vessel 1320. Echoes received by ultrasound probe 1120 from body 1300 are comprised of echoes from tissue 1310 and from blood flow in vessel 1320. These weak ultrasonic echoes are converted to electrical signals by ultrasound probe 1120 and sent, via T/R switch 1110 to AB 1130. AB 1130 outputs an amplified RF signal that is applied as input to detector 1140 and to receivers 1150 and 1155 (in a preferred embodiment, the beamformer in AB 1130 is a digital beamformer and, therefore, AB 1130 includes A/D converters). Detector 1140 outputs a low frequency envelope signal which is extracted from the amplified RF signal, and detector 1140 applies the low frequency envelope signal as input to gray scale scan converter 1160 (GSC 1160). GSC 1160 converts the input into a form appropriate for output display, and GSC 1160 applies the output as input to color display 1170 (CD 1170). CD 1170 displays the scan converted signal in a conventional form as a gray scale display signal.

Since an echo signal from tissue 1310 is usually much stronger than an echo signal from blood flowing in vessel 1320, the gray scale display only shows features of tissue 1310. In order to display features of blood flow in blood vessel 1320, refined processing has to be performed in receivers 1150 and 1155 and color flow processors 1180 and 1185.

Figure 3:
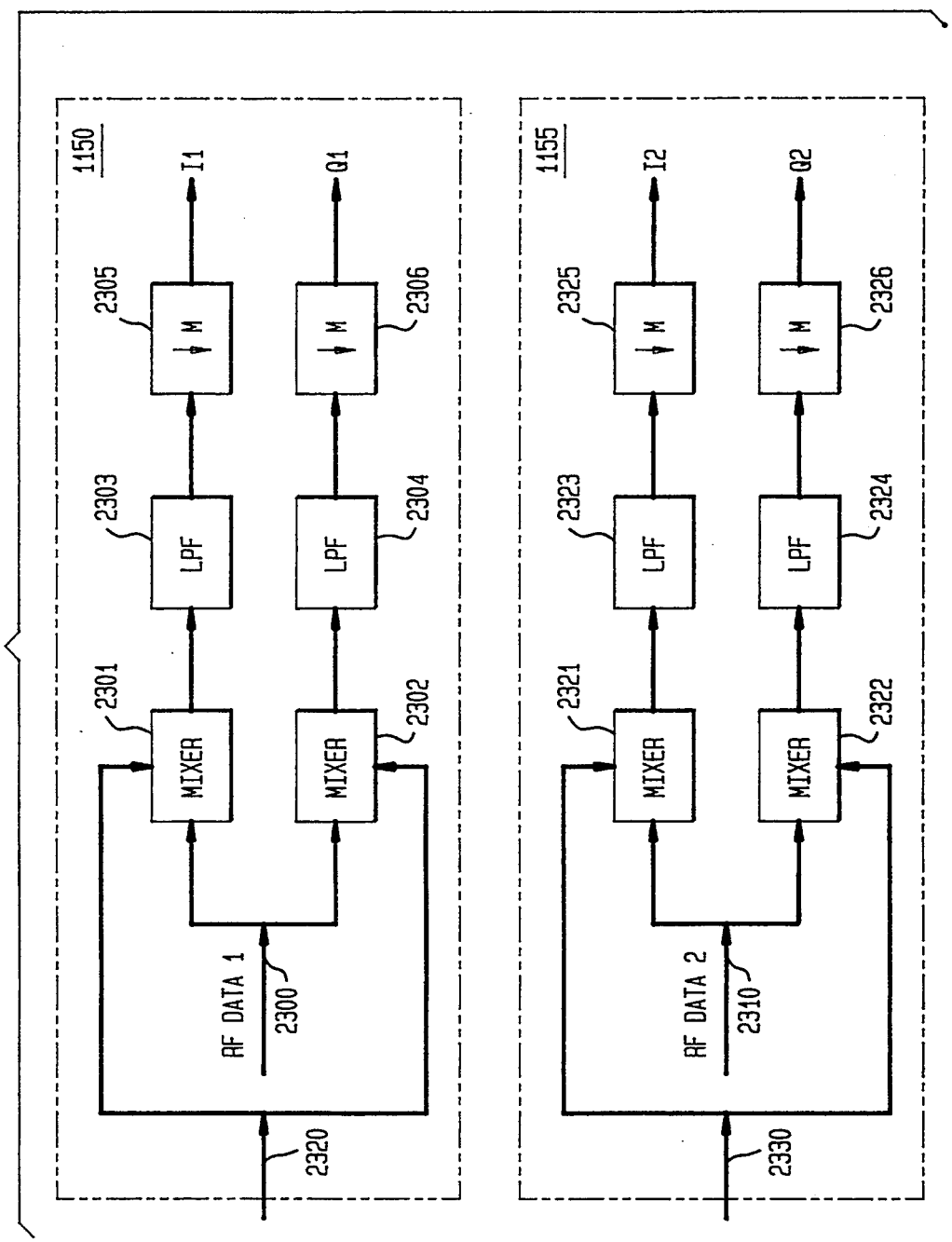
FIG. 3 is a block diagram of data receivers used to fabricate the embodiment of the present invention shown in FIG. 2.

FIG. 3 is a block diagram of (a) receiver 1150 which receives RF data from receive beam 1 (sub-aperture 110) over leads 2300 and (b) receiver 1155 which receives RF data from receive beam 2 (sub-aperture 120)

over leads 2310. RF data 1 is applied as input to mixers 2301 and 2302 (along with a reference signal which is applied as input over lead 2320 from transmitter 1000 to mixers 2301 and 2302) to transfer RF data 1 to baseband and to generate in-phase and quadrature components of the data (generally referred to as I and Q components) in a manner which is well known to those of ordinary skill in the art. Next, the outputs from mixers 2301 and 2302 are applied to low pass filters 2303 and 2304, respectively, to remove image frequency. Next, the outputs from low pass filters 2303 and 2304 are applied as input to decimators 2305 and 2306 to decimate the sample rate by a number M. In a preferred embodiment, the number M should be such that, after decimation, the number of samples per vector is as close as possible to the number of lines occupied by a color flow (CF) image on CD 1170. Finally, I1 and Q1 samples (the in-phase and quadrature components of the data) are applied as input to color flow processor 1180 (CFP 1180) shown in FIG. 4. As further shown in FIG. 3, RF data from receive beam 2 is processed in the same manner as RF data from receive beam 1 is processed.

Figure 4:
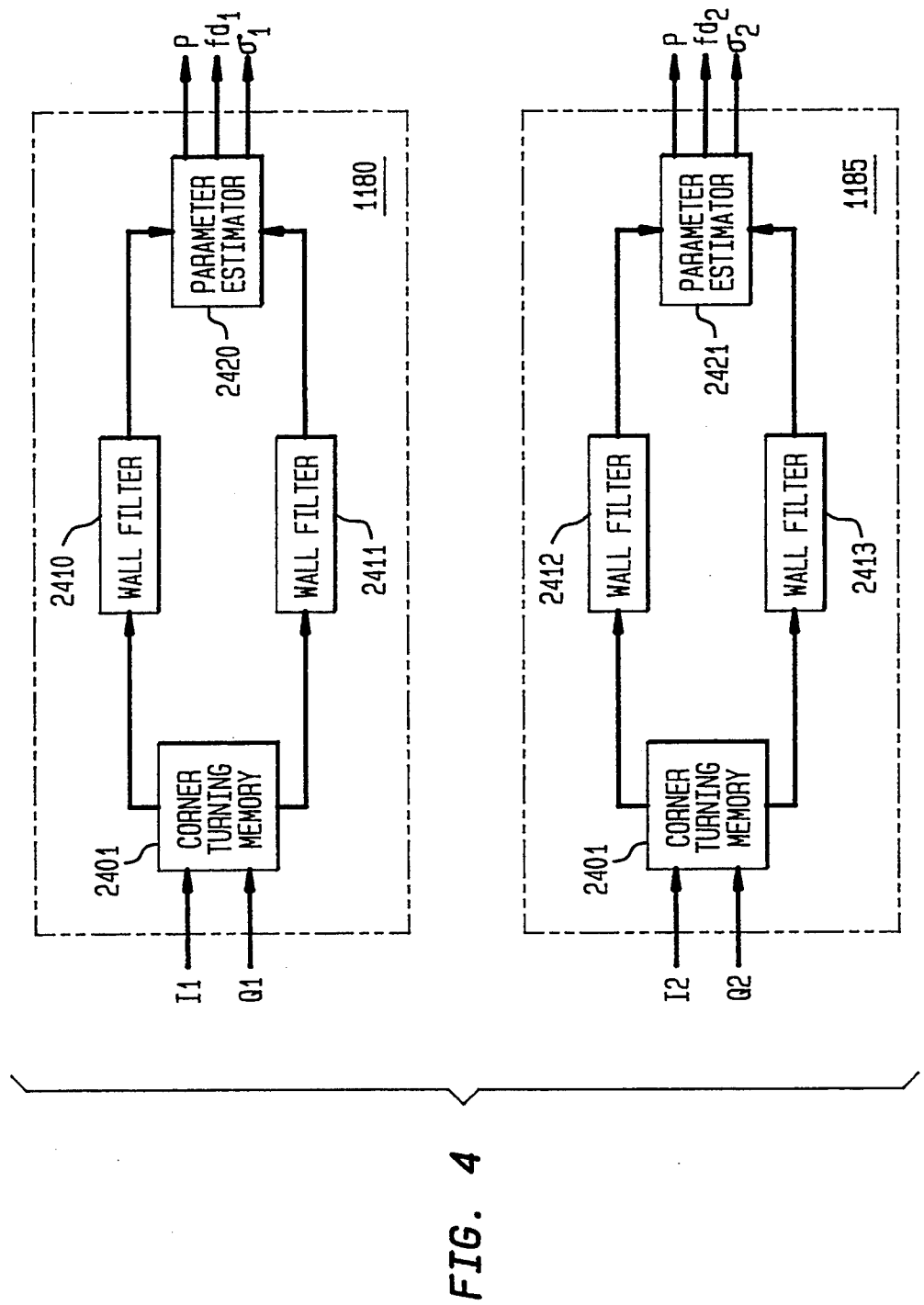
FIG. 4 is a block diagram of color flow processors and a quantitative color flow processor used to fabricate the embodiment of the present invention shown in FIG. 2.

FIG. 4 is a block diagram of CFP 1180 and 1185 and quantitative color flow processor 1190 (QCFP 1190). Referring to FIG. 4, I1 and Q1 samples are applied as input to corner turning memory 2401 (CTM 2401) of CFP 1180. As is known, a corner turning memory performs a mathematical operation of transposition of incoming vectors from an ensemble. As a result, after being processed by a corner turning memory, data are presented rowwise, i.e., an ensemble from depth i is presented after an ensemble from depth i−1. Samples from a given depth are taken at the pulse repetition frequency ("prf"). As is well known in the art, prf represents the rate at which the transducer array can be energized for transmit (1/prf represents the time for a pulse to travel from the transducer to a region of interest and for a reflection therefrom to travel back to the transducer) and, as a consequence of the Nyquist theorem, determines the highest velocity that can be measured without aliasing.

As shown in FIG. 4, I1 and Q1 samples output from CTM 2401 are applied as input to wall filters 2410 and 2411, respectively, where the data is tissue filtered in a manner which is well known to those of ordinary skill in the art to remove reflection from tissue. As further shown in FIG. 4, the wall-filtered I and Q signals for each channel are passed to parameter estimator 2420. Estimator 2420 outputs estimates of three spectral moments of the signal. In most modern ultrasound imaging systems, an auto-correlation first moment estimator, also referred to as a pulse-paired estimator, is utilized to provide this output. A first spectral moment is the power of the signal which is proportional to the backscatter cross-section and the number of scatterers within a resolution volume. A second spectral component is the mean frequency of the signal and is proportional to the mean radial velocity of scatterers within the resolution volume. Finally, a third spectral moment is the spectrum width or variance of the signal which is caused by shear and/or turbulent motion of scatterers within the resolution volume. These estimated parameters are applied as input to QCFP 1190.

QCFP 1190, in combination with predetermined scan geometry parameters (i.e., the R and S parameter values, the angle between the two receive beams, and the transmit beam angle), determines the estimated blood flow angle in blood vessel 1320. The estimated blood flow angle is used to determine an estimate of the magnitude of the blood flow velocity in blood vessel 1320. Then, the power, mean frequency of the signal, variance, and direction of flow at a given pixel are transmitted to quantitative color scan converter 1195 (QCSC 1195). QCSC 1195 scan converts the input and applies the scan converted signals as input to CD 1170 for overlaying of the gray scale signal on CD 1170 in a manner which will be described in detail below. It should be noted that embodiments of the present invention are not limited to cases wherein QCFP 1190 outputs the power, frequency, variance, and direction of blood flow at a given pixel. For example, if QCFP 1190 is an N, D, and P based scan converter as disclosed in U.S. Pat. No. 4,800,891 then N, D, P, and $\theta_i$ will be sent to QCSC 1195 for further processing.

Appendix A describes the method utilized to determine the blood flow angle and the velocity magnitude using the Doppler mean frequency estimates.

Figure 5:
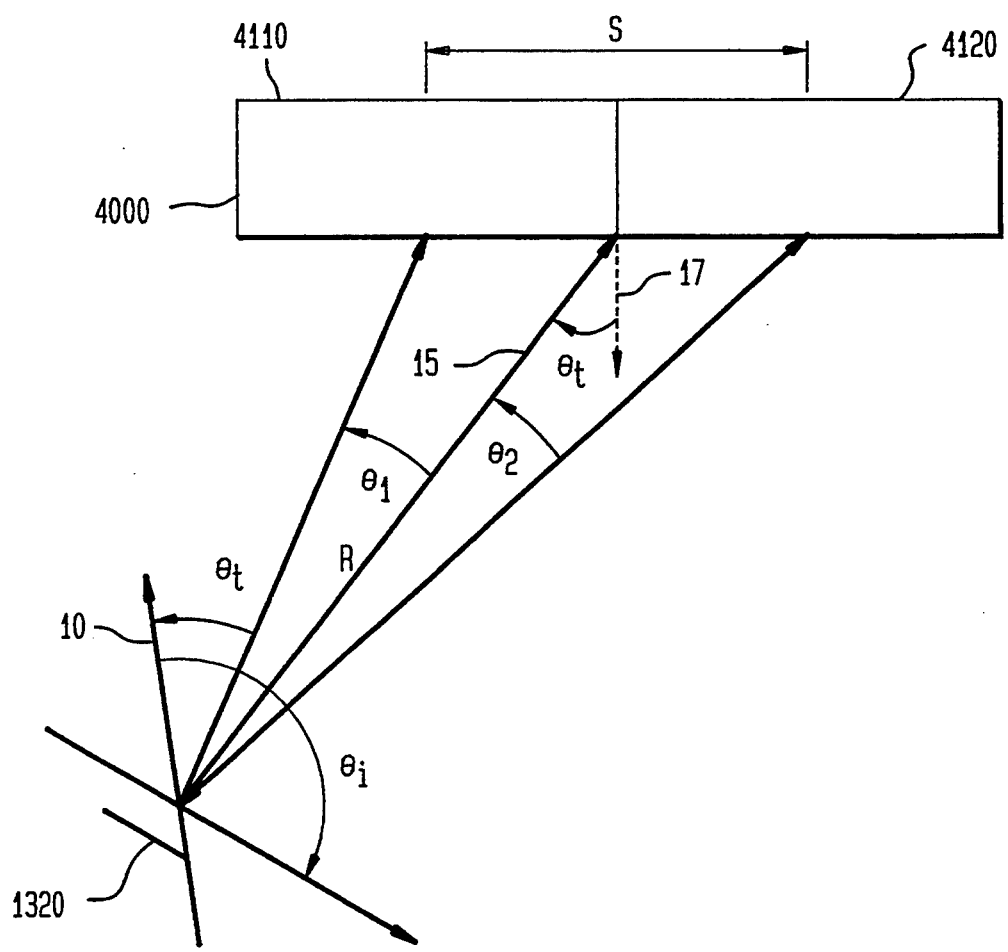
FIG. 5 shows, in pictorial form, a transducer array arrangement for transmit and receive beam geometries used to fabricate embodiments in accordance with a third aspect of the present invention.

FIG. 5 shows, in pictorial form, a transducer array arrangement for transmit and receive beam geometries used to fabricate alternative embodiments of the present invention. As shown in FIG. 5, blood vessel 1320 has blood flowing therethrough with velocity V at an angle $\theta_i$ with respect to arrow 10. In accordance with this aspect of the present invention, transducer 4000 is broken down into sub-apertures 4110 and 4120. A transmit beam is generated utilizing all of transducer array 4000 and receive beams are detected by sub-apertures 4110 and 4120. As further shown in FIG. 5, the centers of sub-apertures 4110 and 4120 are separated by a predetermined distance S and R defines the distance between the center of transducer array 4000 and a sample volume in the blood vessel of interest. The processing of the receive beam data is similar to that shown in FIGS. 3-4 except that the equations are solved as shown in Appendix B.

Figure 6:
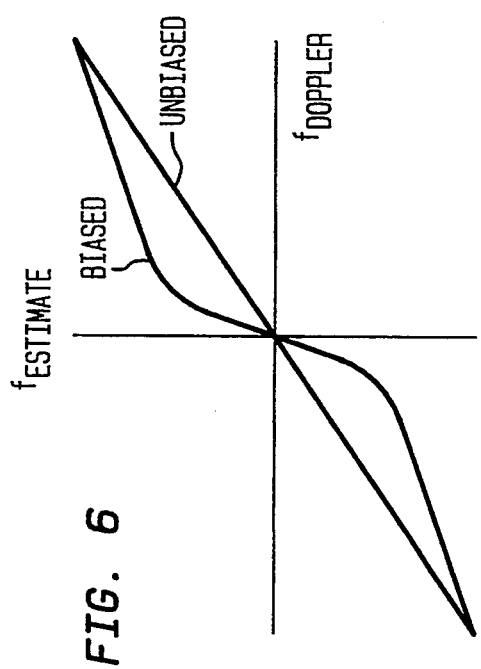
FIG. 6 shows, in graphical form, bias introduced in Doppler frequency estimates by a wall filter.

It is known in the art that an auto-correlation based, first moment estimator is an unbiased estimator. See for example, an article entitled "A covariance approach to spectral moment estimation" by K. S. Miller and M. M. Roshwarger, *IEEE Trans. Inform. Theory*, vol. IT-18, no. 5, 1972, pp. 588-596. However, the use of wall filters (see FIG. 4) to remove tissue echoes (clutter) biases the Pulse-Pair Processor toward higher frequencies. There are two main causes of such bias toward higher frequencies. The first cause of such bias results because the part of the noise spectrum which falls within the stop band of the wall filter is canceled and, correspondingly, white noise is colored. The second cause of such bias is due to the fact that the Doppler signal is a wideband signal and one of the spectral tails will be more or less canceled by a notch filter in the wall filter. This second cause of such bias is dominant at frequencies close to zero. In conventional color flow systems, the use of biased mean frequency estimates does not cause a problem. This is because the estimated Doppler information is shown by means of color maps and the human eye is relatively insensitive to changes in shade produced by the bias. However, in the operation of a dual-beam Doppler mode, bias introduced by the wall filters will cause significant errors during the calculation of a true velocity, which errors are significant around zero frequency. In accordance with the present invention, such errors are corrected in quantitative color flow processor by means of a look-up-table. FIG. 6 shows, in graphical form the bias which is introduced. Values are stored, for example, in a look-up-table so that unbiased estimates of frequency can be provided. Then, the unbiased values are utilized in accordance with the methods shown in Appendices A and B. The specific values utilized depend on the experimentation to calibrate the bias provided by a particular wall filter.

Figure 7:
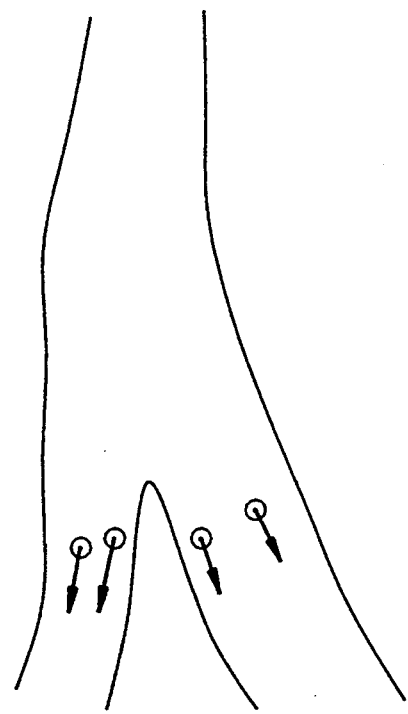
FIG. 7 shows, in pictorial form, a quantitative color flow display provided in accordance with the present invention.

All modern ultrasound imaging systems utilize some kind of temporal velocity color wheel which assumes that flow toward the probe is red whereas flow away from the probe is blue. However, FIG. 7 shows, in pictorial form, a quantitative color flow display provided in accordance with the present invention by QCSC 1195 and CD 1170. As described above, QCFP 1190 estimates the true velocity and corresponding direction of flow in each pixel of a display. Then, in accordance with the present invention, each pixel is assigned its own oriented color map, for example, a color wheel, in accordance with the pixel's maximum velocity over time, which velocity maximum is referred to as a temporal maximum. For example, as shown in FIG. 7, the peak velocity may be assigned to red and reverse velocity may be assigned to blue. Thus, in accordance with this embodiment, direct flow will always be shown as red whereas reverse flow will always be shown as blue, regardless of blood vessel orientation. The temporal maximum is determined for a predetermined time interval, for example, one or two seconds, by examining velocity on a pixel by pixel basis over the time interval in, for example, a buffer memory associated with QCFP 1195. Further, in accordance with the present invention, the time interval utilized may be determined in response to user input. Such user input will be obtained by user interaction with, for example, a terminal (not shown) or a system console and that information will then be applied as input to, for example, QCSC 1195. Still further, in accordance with a further embodiment of the present invention, QCSC 1195 comprises means for providing velocity peak persistence in accordance with methods which are well known to those of ordinary skill in the art for use, on a pixel by pixel basis. QCSC 1195 comprises a frame buffer for use in ascertaining and storing the maximum velocity during the time interval used to provide the display on a pixel basis. Then, after the maximum velocity and its direction are determined, a display is provided for flames contained within the time interval wherein the velocity in each pixel is displayed relative to the color indicator for the maximum velocity and its direction.

Figure 8:
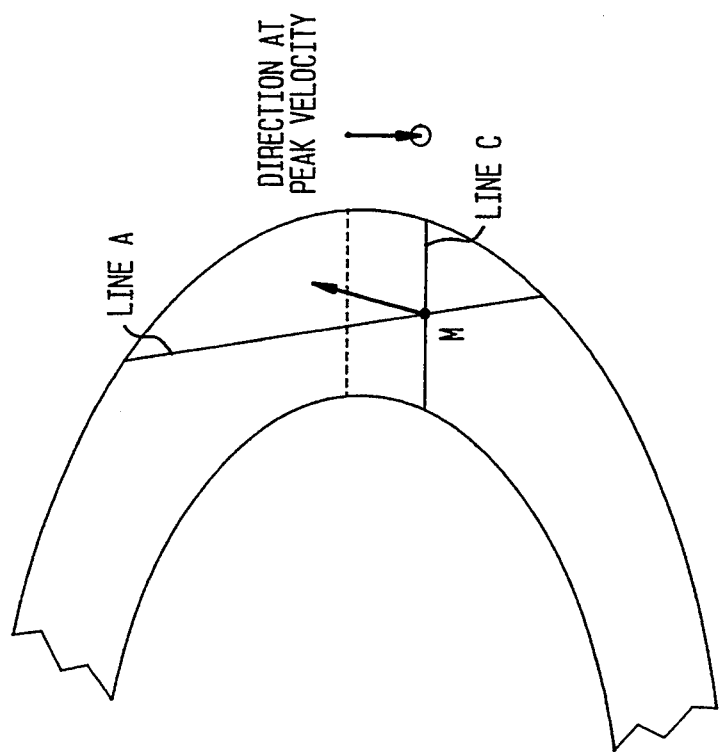
FIG. 8 shows, in pictorial form, a quantitative color flow display in accordance with a further embodiment of the present invention.

FIG. 8 shows, in pictorial form, a quantitative color flow display in accordance with a further embodiment of the present invention which will be referred to as a spatial color wheel. The following steps are carried out in providing the spatial color wheel. First, QCSC 1195 finds a blood vessel. This is done in the preferred embodiment by identifying a predetermined number of adjacent pixels in a line having non-zero velocity, for example, line A in FIG. 8. This ensures that the pixels correspond to a blood vessel. As those of ordinary skill in the art readily appreciate, this step of identifying a blood vessel is done by examining a frame buffer which corresponds to the pixels in the display. Second, QCSC 1195 finds a pixel, for example, pixel M in FIG. 8, in line A which has the maximum velocity of all the pixels on line A over a predetermined time interval. Third, QCSC 1195 identifies a blood vessel cross section, for example, line C in FIG. 8 which is orthogonal to the direction of flow at the velocity peak at the pixel. Fourth, QCSC 1195 moves a pixel up or down from pixel M (either "upstream" or "downstream") and develops a new cross section. This is done in one embodiment as follows. QCSC 1195 moves a pixel up or down from pixel M and identifies another line, like line A, in which all of the pixels have non-zero velocity. Then, as above, QCSC 1195 finds a pixel on this new line which has the maximum velocity of all the pixels on the new line over the predetermined time interval. Then, QCSC 1195 identifies the blood vessel cross section in the manner described above. All pixels in a frame are examined in accordance with the described procedure and assigned to a cross section. The direction of flow of each pixel is coded according to the direction of flow of the pixel in the cross section having the maximal peak velocity. Fifth, QCSC 1195 transmits display information to CD 1170 to display blood flow within each pixel. The direction of flow at each pixel is coded according to the above-described spatial color wheel whereas the value of velocity is displayed by the brightness of color. As a result, and in accordance with the present invention, the spatial color wheel will enable a user to identify branching of blood vessels and to identify turbulent flow caused, for example, by plaque. In a preferred embodiment, a spatial color wheel codes direct flow (flow at 0°) and reverse flow (flow at 180°) as red and blue, respectively, and other directions of flow, for example, flow at 60°, 120°, 240°, and 300°) are coded with other colors, for example, green, yellow, magenta, cyan, and so forth.

In a Power Doppler mode of operation, a color mapping is made by CD 1170 of a power estimate received from QCSC 1195. A power color map is not limited by the cosine of the angle between the blood flow and the transmit beam as was the case for the velocity color map. However, in order to display the power of the blood flow and not the power of the tissue signal, it is necessary to utilize a wall filter. As is known, the wall filter rejects signals from blood flows close to or perpendicular to the receive beam. As a result, the Power Doppler mode of operation in prior art systems are still angle dependent, albeit to a less extent than is the velocity mode of operation. In accordance with the present invention, the Power Doppler mode of operation is made angle independent since one of the two receive beams is not perpendicular to a given blood flow direction. Thus, if one of the beams is close to perpendicular (within a predetermined or user defined threshold), QCFP 1190 utilizes the power estimated from the other beam. It is also important to note that the above-described errors in estimating true velocity would not effect the performance of the system in this mode because true velocity is not displayed.

In accordance with a further embodiment of the present invention, a display is made which utilizes the magnitude of velocity. In such a display, the peak velocity is given a color, for example, red. Then lesser velocities are given other colors which are assigned in accordance with a color wheel which is also displayed. In a preferred embodiment for use in identifying turbulent flow, pixels in the middle of the vessel (presumably having the highest velocity) are displayed with maximal red intensity whereas pixels close to the wall in case of turbulent flow are displayed with different colors.

Although various modifications may be suggested by those versed in the art, it should be understood that we wish to embody within the scope of the patent granted hereon all such modification as reasonably and properly come within the scope of our contribution to the art. For example, although the present invention has been described in turns of a linear transducer array, it should be understood that the present invention is not limited to linear arrays and applies as well to two-dimensional arrays. For example, true velocity measurements in two dimensional arrays would be obtained by breaking the array into a multiplicity of sub-arrays. Then, the displays would be generated in a manner which is substantially like that described above.

Appendix A

The following describes the method utilized to determine the flow angle and the velocity magnitude using the Doppler mean frequency estimates $f_{d1}$ and $f_{d2}$ output as the second spectral components from CF processors 1180 and 1185, respectively. $f_{d1}$ and $f_{d2}$ are given as follows:

$$f_{d2} = 2|V|\cos(\Theta_i + \Theta_t)f_o/c \tag{1}$$

$$f_{d1} = |V|[\cos(\Theta_i + \Theta_t) + \cos(\Theta_i + \Theta_t + \Theta_a)]f_o/c \tag{2}$$

where $f_o$ is the transmit frequency, c is the speed of sound, $|V|$ is the magnitude of the flow velocity, blood flow is at angle $\Theta_i$ with respect to arrow 10 shown in FIG. 1, the transmit and receive beam of sub-aperture 120 occur at angle $\Theta_t$ with respect to arrow 20 shown in FIG. 1, and $\Theta_a$ is the angle between the two receive beams shown in FIG. 1. $\Theta_a$ can be expressed as follows:

$$\Theta_a = \sin^{-1}[S\cos(\Theta_t)/(R^2 + S^2 + 2RS\sin(\Theta_t))^{\frac{1}{2}}] \tag{3}$$

where S is the distances between the centers of sub-aperture arrays 110 and 120 shown in FIG. 1 and R is range distance from the center of sub-aperture 120 and the sample volume in blood vessel 1320. Eqn. (1) and (2) are solved to provide the blood flow angle $\Theta_i$ and velocity magnitude $|V|$ which are expressed as follows:

$$\Theta_i = \tan^{-1}[(1 + \cos(\Theta_a) - 2f_{d1}/f_{d2})/\sin(\Theta_a)] - \Theta_t \tag{4}$$

$$|V| = (f_{d2}\,c)/(2f_o\cos(\Theta_i + \Theta_t)) \tag{5}$$

In eqn. (4), the signs of $f_{d1}$ and $f_{d2}$ are lost during the division of $f_{d1}/f_{d2}$. Therefore, eqn. (4) is valid only for $f_{d2} > 0$, i.e., for 180 degrees of the possible 360 degrees of flow. The corrected angle, i.e., the estimate of the direction of flow which is valid for all 360 degrees is given by:

$$\Theta_{icorr} = \begin{cases} \Theta_i & \text{for } f_{d2} > 0 \\ \Theta_i - 180° & \text{for } f_{d2} < 0 \text{ and } \Theta_i > 0 \\ \Theta_i + 180° & \text{for } f_{d2} < 0 \text{ and } \Theta_i \leq 0 \end{cases} \tag{6}$$

However, there are four cases to consider. In case 1, if the direction of blood flow is not perpendicular or close to perpendicular to either of the two receive beams, then the direction of blood flow can be determined using eqn. (6). In case 2, if both abs($f_{d1}$) and abs($f_{d2}$) are zero or below a user defined frequency threshold, then it can be assumed that the true Doppler frequency shift is zero and no angle needs to be calculated.

In case 3, if the estimate $f_{d2}$ is effectively zero, i.e., smaller than a user defined frequency threshold, and abs($f_{d1}$) is larger than the user defined frequency threshold, the direction of blood flow is given by:

$$\Theta_{icorr} = \begin{cases} -90° - \Theta_t & \text{for } f_{d1} > 0 \\ +90° - \Theta_t & \text{for } f_{d1} < 0 \end{cases} \tag{7}$$

In case 4, if the estimate $f_{d1}$ is effectively zero, i.e., smaller than a user defined frequency threshold, and abs($f_{d2}$) is larger than the above-mentioned user defined frequency threshold, the direction of blood flow is given by:

$$\Theta_{icorr} = \begin{cases} -90° - \Theta_t + \Theta_a/2 & \text{for } f_{d2} > 0 \\ +90° - \Theta_t + \Theta_a/2 & \text{for } f_{d2} < 0 \end{cases} \tag{8}$$

The accuracy of the above calculation depends mostly on the quality of the mean Doppler frequency estimator. In the preferred embodiment an auto-correlation-based algorithm is utilized to obtain estimates of mean Doppler frequency, $f_{est}$, from the first lag of the complex auto-correlation. The real and imaginary parts, respectively, of the first lag auto-correlation are given as:

$$X = \sum_{n=2}^{M} [Q(n)I(n-1) - Q(n-1)I(n)] \tag{9}$$

$$Y = \sum_{n=2}^{M} [I(n)I(n-1) + Q(n)Q(n-1)]$$

where the sums are from n=2 to n=M (M is the number of accumulated I(n) and Q(n) samples) and I(n) and Q(n) are the nth samples of the I and Q components for each channel. As discussed above, due to decimation and accumulation, the samples are at the pulse repetition rate. $f_{est}$ is obtained as follows:

$$f_{est} = (\tfrac{1}{2}\pi)\tan^{-1}(X/Y) \tag{10}$$

Appendix B

Analysis using a full aperture transmit as indicated in FIG. 5.

$$f_{d2} = |V|[\cos(\Theta_i + \Theta_t) + \cos(\Theta_i + \Theta_t + \Theta_2)]f_o/c \tag{18}$$

$$f_{d1} = |V|[\cos(\Theta_i + \Theta_t) + \cos(\Theta_i + \Theta_t + \Theta_1)]f_o/c \tag{19}$$

where $f_o$ is the transmit frequency, c is the speed of sound, $|V|$ is the magnitude of the flow velocity, blood flow is at angle $\Theta_i$ with respect to arrow 10 shown in FIG. 5, the receive beam of sub-aperture 120 occurs at angle $\Theta_2$ with respect to arrow 15 shown in FIG. 5, the receive beam of sub-aperture 110 occurs at angle $\Theta_1$ with respect to arrow 15 shown in FIG. 5, and the transmit beam of transducer array 1000 occurs at angle $\Theta_t$ with respect to arrow 17 shown in FIG. 5. Blood flow angle $\Theta_i$ and velocity magnitude $|V|$ can be expressed as follows:

$$zn = f_{d1}(1 + \cos(\Theta_2)) - f_{d2}(1 + \cos(\Theta_1))$$

$$zd = f_{d1}\sin(\Theta_2) - f_{d2}\sin(\Theta_1)$$

$$\Theta_i = \tan^{-1}[zn/zd] - \Theta_t \tag{20}$$

$$|V| = (f_{d2}\,c)/[\cos(\Theta_i + \Theta_t) + \cos(\Theta_i + \Theta_t + \Theta_2)] \tag{21}$$

As was discussed above with respect to the first and second aspects of the present invention, a corrected angle $\Theta_{icorr}$, i.e., the estimate of the direction of flow which is valid for all 360 degrees is given by:

$$\Theta_{icorr} = \begin{cases} \Theta_i & \text{for } f_{d2} > 0 \\ \Theta_i - 180° & \text{for } f_{d2} < 0 \text{ and } \Theta_i > 0 \\ \Theta_i + 180° & \text{for } f_{d2} < 0 \text{ and } \Theta_i \leq 0 \end{cases} \quad (22)$$

However, again, there are four cases to consider. In case 1, if the direction of blood flow is not perpendicular or close to perpendicular to either of the two receive beams, then the direction of blood flow can be determined using eqn. (6). In case 2, if both abs($f_{d1}$) and abs($f_{d2}$) are zero or below a user defined frequency threshold, then it can be assumed that the true Doppler frequency shift is zero and no angle needs to be calculated.

In case 3, if the estimate $f_{d2}$ is effectively zero, i.e., smaller than a user defined frequency threshold, and abs($f_{d1}$) is larger than a user defined frequency threshold, the direction of blood flow is given by:

$$\Theta_{icorr} = \begin{cases} -90° - \Theta_t - \Theta_2/2 & \text{for } f_{d1} > 0 \\ +90° - \Theta_t + \Theta_2/2 & \text{for } f_{d1} < 0 \end{cases} \quad (23)$$

In case 4, if the estimate $f_{d1}$ is effectively zero, i.e., smaller than a user defined frequency threshold, and abs($f_{d2}$) is larger than the above-mentioned user defined frequency threshold, the direction of blood flow is given by:

$$\Theta_{icorr} = \begin{cases} -90° - \Theta_t + \Theta_2 + \Theta_1/2 & \text{for } f_{d2} > 0 \\ +90° - \Theta_t + \Theta_2 + \Theta_1/2 & \text{for } f_{d2} < 0 \end{cases} \quad (24)$$

The rest of the processing to provide the blood flow velocity distribution and display of blood flow angle proceed in similar fashion as has been described above with respect the embodiment shown in FIGS. 1–4.

What is claimed is:

1. A method for providing a quantitative color flow display of moving matter using an ultrasound imaging system, the display being formed of pixels on a display device, which method comprises the steps of:
   transmitting acoustic beams to a region of interest in the body, which region of interest includes the moving matter;
   receiving echo beams from the region of interest;
   obtaining, at each portion of the region of interest, which portion is referred to as a pixel, a measure of velocity of moving matter in the pixel and a measure of direction of the velocity of the moving matter in the pixel;
   determining a maximum of the measure of velocity at each pixel in the region of interest over a predetermined period of time and the measure of direction of the maximum velocity; and
   displaying the measures of velocity of the pixels for the predetermined period of time wherein the measures of velocity and the measure of direction of the velocity are displayed using a color indicator which is relative to the maximum measure of velocity at each pixel and to the measure of direction of the maximum velocity.

2. The method of claim 1 wherein the color indicator comprises a circle of colors wherein velocity at the value of the maximum and in the same direction as the maximum is a first color and other values of velocity and direction have different color.

3. The method of claim 2 wherein the first color is red and a velocity in a direction opposite to the direction of the maximum velocity is blue.

4. A method for providing a quantitative color flow display of moving matter using an ultrasound imaging system, the display being formed of pixels on a display device, which method comprises the steps of:
   transmitting acoustic beams to a region of interest in the body, which region of interest includes the moving matter;
   receiving echo beams from the region of interest;
   obtaining, at each portion of the region of interest, which portion is referred to as a pixel, a measure of power of the echo beam from the pixel;
   determining a maximum of the measure of power at each pixel in the region of interest over a predetermined period of time; and
   displaying the measures of power of the pixels for the predetermined period of time using a color indicator which is relative to the maximum power at each pixel.

5. The method of claim 4 wherein the color indicator comprises a circle of colors wherein power at the value of the maximum is a first color and other values of power have one or more different colors.

6. The method of claim 5 wherein the first color is red.

7. A method for providing a quantitative color flow display of moving matter using an ultrasound imaging system, the display being formed of pixels on a display device, which method comprises the steps of:
   transmitting acoustic beams to a region of interest in the body, which region of interest includes the moving matter;
   receiving echo beams from the region of interest;
   obtaining, at each portion of the region of interest, which portion is referred to as a pixel, a measure of velocity of moving matter in the pixel;
   determining a maximum of the measure of velocity in the pixels in the region of interest over a predetermined period of time; and
   displaying the measures of velocity of the pixels for the predetermined period of time using a color indicator which is relative to the maximum of the measures.

8. The method of claim 7 wherein the color indicator comprises a circle of colors wherein velocity at the value of the maximum is a first color and other values of velocity have different colors.

9. The method of claim 8 wherein the first color is red.

10. A method for providing a quantitative color flow display of moving matter using an ultrasound imaging system, the display being formed of pixels on a display device, which method comprises the steps of:
    transmitting acoustic beams to a region of interest in the body, which region of interest includes the moving matter;
    receiving echo beams from the region of interest;

obtaining, at each portion of the region of interest, which portion is referred to as a pixel, a measure of velocity of moving matter in the pixel and a measure of direction of the velocity of the moving matter in the pixel;

determining a cross section of the moving matter from the measures of velocity of the moving matter in the pixels in the region of interest;

determining a maximum of the measures of velocity in the cross section;

displaying the measures of velocity and direction of the pixels of the cross section wherein the measures of direction are displayed using a color indicator which is relative to the direction of the maximum measure of velocity in the cross section and wherein the measures of velocity are displayed in intensity relative to the maximum measure of velocity.

11. The method of claim 10 wherein the color indicator comprises a circle of colors wherein a direction in the same direction as the maximum is a first color and other values of direction have different colors.

12. The method of claim 11 wherein the first color is red and a velocity in a direction opposite to the direction of the maximum velocity is blue.

13. A method for providing a quantitative color flow display of blood flow in a blood vessel using an ultrasound imaging apparatus, which method comprises the steps of:

transmitting an acoustic beam to a region of interest in the blood vessel from a first sub-aperture array in a transducer array;

receiving a first echo beam from the region of interest at the first sub-aperture array, which first echo beam is generated by the acoustic beam, and a second echo from the region of interest at a second sub-aperture array, which second echo beam is generated by the acoustic beam;

estimating a first mean Doppler frequency from the first echo beam in a color flow processor substantially in parallel with the step of estimating a second mean Doppler frequency from the second echo beam in a color processor;

estimating a blood flow angle and blood flow velocity in the region of interest in the blood vessel from the first and second mean Doppler frequencies;

converting the data to provide a blood flow velocity distribution; and;

displaying (a) the blood flow velocity distribution in accordance with a color indicator and (b) displaying the color indicator so that it indicates the direction of the estimate of blood flow angle.

14. The method of claim 13 Wherein the color indicator is a color bar comprised of two colors, a first color for flow in the direction of the estimated angle and a second color for flow in the opposite direction.

15. The method of claim 14 wherein the color indicator is a color wheel having a line indicator of the direction.

16. The method of claim 13 which further comprises the step of displaying a warning when an estimate of blood flow angle, relative to the transmitted acoustic beam, exceeds a predetermined value.

17. The method of claim 16 wherein the warning comprises flashing the region of interest.

18. A method for providing a quantitative color flow display of blood in a blood vessel using an ultrasound imaging apparatus, which method comprises the steps of:

transmitting an acoustic beam to a region of interest in the blood vessel from a transducer array;

receiving a first echo beam from the region of interest at the transducer array, which first echo beam is generated by the acoustic beam, and a second echo from the region of interest at the transducer array, which second echo beam is generated by the acoustic beam;

estimating a first mean Doppler frequency from the first echo beam in a color flow processor substantially in parallel with the step of estimating a second mean Doppler frequency from the second echo beam in a color processor;

estimating a blood flow angle and blood flow velocity in the region of interest in the blood vessel from the first and second mean Doppler frequencies;

converting the data to provide a blood flow velocity distribution; and;

displaying (a) the blood flow velocity distribution in accordance with a color indicator and (b) displaying the color indicator so that it indicates the direction of the estimate of blood flow angle.

19. The method of claim 18 wherein the steps of estimating comprise the steps of wall filtering and compensating the estimates for biasing which results from wall filtering.

20. A method for providing a quantitative color flow display of blood in a blood vessel using an ultrasound imaging apparatus, which method comprises the steps of:

transmitting an acoustic beam to a region of interest in the blood vessel from a transducer array;

receiving a first echo beam from the region of interest at the transducer array, which first echo beam is generated by the acoustic beam, and a second echo from the region of interest at the transducer array, which second echo beam is generated by the acoustic beam;

estimating a first mean Doppler frequency and a first power from the first echo beam in a color flow processor substantially in parallel with the step of estimating a second mean Doppler frequency and a second power from the second echo beam in a color processor;

estimating a blood flow angle in the region of interest in the blood vessel from the first and second mean Doppler frequencies;

determining the angle of the first echo beam and the second echo beam with respect to the estimated blood flow angle;

converting the data to provide color power distribution data selected from a predetermined one of the first power or second power;

utilizing the non-selected power whenever the angle of the selected one of the first power or second power was determined from an echo beam having an angle whose value is within a predetermined amount from 90°; and;

displaying the color power distribution data.

21. A method for providing a blood flow velocity distribution display of blood in a blood vessel using an ultrasound imaging apparatus, which method comprises the steps of:

transmitting an acoustic beam to a region of interest in the blood vessel from a first sub-aperture array in a transducer array;

receiving a first echo beam from the region of interest at the first subaperture array, which first echo beam is generated by the acoustic beam, and a second echo from the region of interest at a second sub-aperture array, which second echo beam is generated by the acoustic beam;

estimating a first mean Doppler frequency from the first echo beam in a color flow processor substantially in parallel with the step of estimating a second mean Doppler frequency from the second echo beam in a color flow processor;

estimating a first blood flow angle in the region of interest in the blood vessel from the first and second mean Doppler frequencies;

transmitting a second acoustic beam to a region of interest in the blood vessel from the second sub-aperture array;

receiving a third echo beam from the region of interest at the second sub-aperture array, which third echo beam is generated by the second acoustic beam;

estimating a third mean Doppler frequency from the third echo beam in a color flow processor;

estimating a second blood flow angle in the region of interest in the blood vessel from the first and third mean Doppler frequencies; and comparing the first and second blood flow angles and displaying a warning if the values differ by more than a predetermined amount.

22. A method for providing a blood flow velocity distribution display of blood in a blood vessel using an ultrasound imaging apparatus, which method comprises the steps of:

transmitting an acoustic beam to a region of interest in the blood vessel from a transducer array;

receiving a first echo beam from the region of interest at a first sub-aperture array, which first echo beam is generated by the acoustic beam, and a second echo from the region of interest at a second sub-aperture array, which second echo beam is generated by the acoustic beam;

estimating a first mean Doppler frequency from the first echo beam in a color flow processor substantially in parallel with the step of estimating a second mean Doppler frequency from the second echo beam in a color flow processor;

estimating a blood flow and blood flow velocity in the region of interest in the blood vessel from the first and second mean Doppler frequencies;

converting the data to provide a blood flow velocity distribution; and;

displaying (a) the blood flow velocity distribution in accordance with a color bar and (b) displaying the color bar so that it is oriented along the direction of the estimate of blood flow angle.

23. Ultrasound imaging system for providing a quantitative color flow display of moving matter, the display being formed of pixels on a display device, which system comprises:

means for transmitting acoustic beams to a region of interest in the body, which region of interest includes the moving matter, and for receiving echo beams from the region of interest;

means for obtaining, at each portion of the region of interest, which portion is referred to as a pixel, a measure of velocity of moving matter in the pixel and a measure of direction of the velocity of the moving matter in the pixel;

means for determining a maximum of the measure of velocity at each pixel in the region of interest over a predetermined period of time and the measure of direction of the maximum velocity; and means for displaying the measures of velocity of the pixels for the predetermined period of time wherein the measures of velocity and the measure of direction of the velocity are displayed using a color indicator which is relative to the maximum measure of velocity at each pixel and to the measure of direction of the maximum velocity.

* * * * *